United States Patent
Wang et al.

(10) Patent No.: US 10,603,133 B2
(45) Date of Patent: Mar. 31, 2020

(54) IMAGE GUIDED AUGMENTED REALITY METHOD AND A SURGICAL NAVIGATION OF WEARABLE GLASSES USING THE SAME

(71) Applicant: TAIWAN MAIN ORTHOPAEDIC BIOTECHNOLOGY CO., LTD., Taichung (TW)

(72) Inventors: Min-Liang Wang, Taichung (TW); Pei-Yuan Lee, Taichung (TW); Ming-Hsien Hu, Taichung (TW)

(73) Assignee: Taiwan Main Orthopaedic Biotechnology Co., Ltd., Taichung (TW)

( * ) Notice: Subject to any disclaimer, the term of this patent is extended or adjusted under 35 U.S.C. 154(b) by 0 days.

(21) Appl. No.: 16/316,623

(22) PCT Filed: Jul. 11, 2016

(86) PCT No.: PCT/CN2016/000374
§ 371 (c)(1),
(2) Date: Jan. 10, 2019

(87) PCT Pub. No.: WO2018/010040
PCT Pub. Date: Jan. 18, 2018

(65) Prior Publication Data
US 2019/0216572 A1    Jul. 18, 2019

(51) Int. Cl.
*A61B 90/00* (2016.01)
*A61B 34/20* (2016.01)
(Continued)

(52) U.S. Cl.
CPC .............. *A61B 90/36* (2016.02); *A61B 34/20* (2016.02); *G06F 3/013* (2013.01); *G06T 7/73* (2017.01);
(Continued)

(58) Field of Classification Search
CPC . A61B 34/20; A61B 90/36; A61B 2034/2057; A61B 2034/256;
(Continued)

(56) References Cited

U.S. PATENT DOCUMENTS 8,648,897 B2* 2/2014 Dobbie ................ G02B 27/017
348/43

FOREIGN PATENT DOCUMENTS

CN      101163236 A     4/2008
WO      2015/126466 A1  8/2015

* cited by examiner

*Primary Examiner* — Charles V Hicks
(74) *Attorney, Agent, or Firm* — Pai Patent & Trademark Law Firm; Chao-Chang David Pai

(57) ABSTRACT

This present invention discloses an image guided augmented reality method, comprising the following steps of: obtaining a first conversion matrix of a camera and a marked point; obtaining a second conversion matrix of the eye and the camera; linking the first conversion matrix and the second conversion matrix to obtain a correct position corresponding matrix of the eye to the marked point; and linking the correct position corresponding matrix to a position feature of the marked point to obtain the correct position of the eye to the marked point. The present invention also discloses a surgical navigation method of wearable glasses, used for obtaining the correct position of the operator's eye to the marked point.

10 Claims, 1 Drawing Sheet

(51) Int. Cl.
  *G06T 15/00* (2011.01)
  *G06T 7/73* (2017.01)
  *G06F 3/01* (2006.01)
  *A61B 34/00* (2016.01)
  *A61B 90/50* (2016.01)

(52) U.S. Cl.
  CPC ...... *G06T 15/00* (2013.01); *A61B 2034/2057* (2016.02); *A61B 2034/256* (2016.02); *A61B 2090/365* (2016.02); *A61B 2090/374* (2016.02); *A61B 2090/3762* (2016.02); *A61B 2090/502* (2016.02); *G06T 2207/30204* (2013.01)

(58) Field of Classification Search
  CPC ........ A61B 2090/365; A61B 2090/374; A61B 2090/3762; A61B 2090/502; G06F 3/013; G06F 7/73; G06F 15/00; G06F 2207/30204
  See application file for complete search history.

IMAGE GUIDED AUGMENTED REALITY METHOD AND A SURGICAL NAVIGATION OF WEARABLE GLASSES USING THE SAME

BACKGROUND OF THE INVENTION

1. Field of the Invention

The present invention relates to an image guided augmented reality method, and more particularly to a surgical navigation of wearable glasses using the image guided augmented reality method.

2. Description of the Related Art

In recent years, with the development of new health care technology, computer-assisted surgery has increased significantly. Since the accuracy of surgical instruments and imaging technology has improved, doctors not only can enhance the quality of their surgery, but also can minimize patient wounds. Generally, a computer-assisted surgery consists of four parts: acquiring images from a patient, image analysis and processing, pre-diagnosis and surgical planning simulation, and finally receiving the surgery guidance for the patient. Computer-assisted surgery of the surgery currently is divided into the following steps: first, using tomography images, including computerized tomography (CT), magnetic resonance imaging (MRI), X ray, nuclear medicine imaging, reconstructed 3D models (non-real-time image), and second: using the mobile C-arm X-ray machine or ultrasound imaging in the operating room as an auxiliary guide (real-time image) and a non-image-based guidance system.

Clinical application of image guided surgical systems, including spinal surgery guide (e.g., pedicle screw fixation, removal of damaged sites, removal of lumps, and disposing electrode to a fixed depth for epilepsy patients); head lesion surgery (e.g., treatment of meningioma, craniopharyngioma, chondrosarcoma, and other lesions in the cranial portion); tumor resection tissue sections; treatment of Parkinson's disease; treatment of huibu brain stereotaxic of psychiatric disorders; audition functional sinus surgery; neurovascular surgical repair and ventricular bypass surgery and ventricular shunt replacement surgery. This system can also be used for the hip and knee surgery, such as total knee arthroplasty, total hip replacement surgery, and anterior cruciate ligament reconstruction.

Operation must be combined with image guide, electronic, machinery, and other techniques, so the orientation of the surgical instrument projected onto the image may assist a physician to grasp the relative orientation between the device and the patient and to achieve the purpose of navigation. Before the operation, the doctor first puts a mark on the patient's surgical site, and then allows the patient to undergo a computerized tomography or magnetic resonance imaging examination. The image of computerized tomography or magnetic resonance image is reconstructed in the computer to form the three-dimensional position near the surgical site, and the location of the anomaly and normal functional area are indicated. At the time of surgery, surgical site of the patient and the surgical instruments have mounting marks, and then infrared camera (ultrasound or the like) can label the localization and relative positions of the surgical site and the surgical instrument simultaneous to create space surgery relationship according to these infrared signals reflected from the mark. In addition, the surgeon may use the head or heads-up display through the eyepiece to see the image reorganization.

Augmented Reality (Augmented Reality, AR) and Mixed Reality (Mixed Reality, MR) are generally used to display virtual information on the real image of the patient. Particularly in minimally invasive surgery using the endoscope in the past, the overlay of images is performed in the augmented and mixed reality images. This way can not be directly observed by the camera, but now the image can be seen prior to surgery. Augmented and mixed reality assist the surgeon to see through the patient's body part, so that the doctor prior to the surgical site visits, vital structures thereof can be effectively positioned without confirming the position beforehand by performing the operation. Augmented and mixed reality technology seems to be currently the most promising research, which helps guide the surgeon and process supervision robotic surgery.

In the surgical site, the marked point is conventionally positioned by the tracking probe for physical space, and the marked point of surgical site is aligned by the least square method. The most common 3D to 2D marked points of surgical site are based primarily on the function of specific surface features. The surface of the surgical site is segmented by the pre-operative image and the contour captured by the intraoperative image, and recorded in such a way that the distance is minimized according to the cost function. The choice of contour is rather cumbersome and time consuming, so a reference mark such as a metal needle or mesh is needed to align the surgical site with the marked points for image guided treatment. A number of methods have been developed to address the problem of posture assessment of pre-operative imaging devices in which image ray is assumed to intersect at a common point. Research has been conducted on image basic issues in the past. Closed-form solutions have been developed to confirm whether three or four sets of 3D/2D correspondences are used.

In view of the above problems, it is necessary to propose a more precise surgical guidance. In this patent, an image guided augmented reality method is mainly proposed, in particular, the method is applied to Augmented Reality Computer Assisted Glasses for Orthopaedic (ARCAGO).

BRIEF SUMMARY OF THE INVENTION

An object of the present invention is to provide an image guided augmented reality method, used for obtaining a correct position of an eye to a marked point, the image guided augmented reality method comprising the following steps of: obtaining a first conversion matrix of a camera and a marked point; obtaining a second conversion matrix of the eye and the camera; linking the first conversion matrix and the second conversion matrix to obtain a correct position corresponding matrix of the eye to the marked point; and linking the correct position corresponding matrix to a position feature of the marked point to obtain the correct position of the eye to the marked point.

According to one aspect of the present invention, obtaining the first conversion matrix uses a first library to detect the position feature of the marked point and uses a first mathematical operation for the position feature of the marked point to obtain the first conversion matrix.

According to one aspect of the present invention, obtaining the second conversion matrix of the eye and the camera further comprises the following steps of: wearing a glasses and selecting a plurality of corner points of the marked point to obtain a two-dimensional coordinate on a screen of the glasses; using a second library to obtain a three-dimensional coordinate corresponding to the camera, to obtain the second conversion matrix of two-dimensional coordinate and the camera by a second mathematical operation; and using a de-coupling equation to obtain the second conversion matrix.

According to one aspect of the present invention, the plurality of corner points of the marked point are 12 corner points.

An object of the present invention is to provide a surgical navigation method of wearable glasses, comprising the following steps of: before the operation, making a tomographic image of more than one marked point in the affected part; making the tomographic image into a three-dimensional stereoscopic simulated image; using an image guided augmented reality method to obtain a correct position of an operator's eye to the marked point of the affected part to adjust the error of the three-dimensional stereoscopic image and the marked point; wherein the image guided augmented reality method comprises the following steps of: obtaining a first conversion matrix of a camera and a marked point; obtaining a second conversion matrix of the eye and the camera; linking the first conversion matrix and the second conversion matrix to obtain a correct position corresponding matrix of the eye to the marked point; and linking the correct position corresponding matrix to a position feature of the marked point to obtain the correct position of the eye to the marked point.

According to one aspect of the present invention, obtaining the first conversion matrix uses a first library to detect the position feature of the marked point and uses a first mathematical operation for the position feature of the marked point to obtain the first conversion matrix.

According to one aspect of the present invention, obtaining the second conversion matrix of the eye and the camera further comprises the following steps of: wearing a glasses and selecting a plurality of corner points of the marked point to obtain a two-dimensional coordinate on a screen of the glasses; using a second library to obtain a three-dimensional coordinate corresponding to the camera, to obtain the second conversion matrix of two-dimensional coordinate and the camera by a second mathematical operation; and using a de-coupling equation to obtain the second conversion matrix.

According to one aspect of the present invention, the plurality of corner points of the marked point are 12 corner points.

DETAILED DESCRIPTION OF THE INVENTION

While the present invention can be applied in different forms of embodiment, the drawings and the following description are merely of preferred embodiments of the present invention by way of examples, and are not intended to limit the invention to the illustrated and/or described in a particular embodiment.

The present invention provides an image guided augmented reality method, which can be applied to Augmented Reality Computer Assisted Glasses for Orthopaedic (ARCAGO). The present invention mainly solves the recording method relating to the application of a three-dimensional model to surgery, and uses a three-dimensional model captured from a CT pre-operative image. We will consider the use of image guided augmented reality techniques in surgery and the basic imaging methods using 3D-3D posture recording. Once the posture is recorded, the augmented reality can be viewed as a mixture of virtual and real environmental spaces that simultaneously reproduce the patient's information.

Because the visual focus of the human eye as seen from the glasses has an error value from the distance of the actual object from the eye, the present invention would solve this problem. The first part is the camera obtains a position of the marked point, and the second part is the calibration of the position error value of a surgical operator's eye 30 to the marked point.

Figure 1:
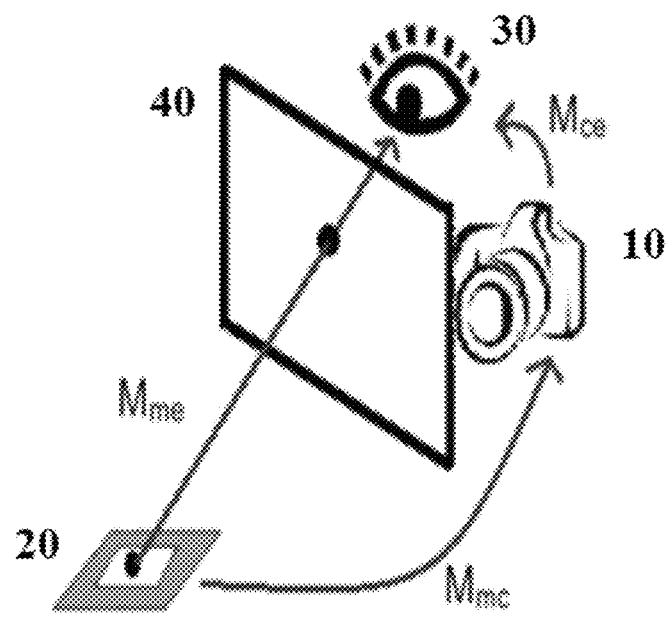
FIG. 1 is a system architecture of the image guided augmented reality method and the surgical navigation of wearable glasses using the image guided augmented reality method according to the present invention.
Figure 2:
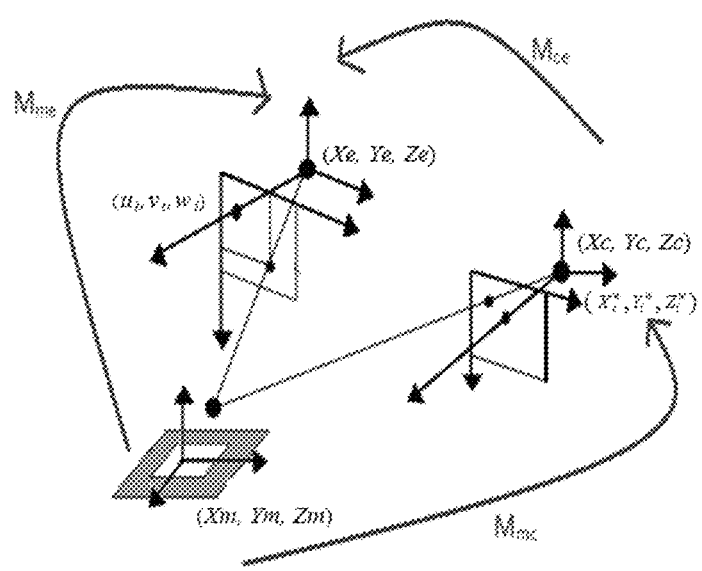
FIG. 2 is a diagram showing the coordinate relationship of the system architecture of FIG. 1 of the present invention.

Please referring to FIG. 1, it is a system architecture of the image guided augmented reality method and the surgical navigation of wearable glasses using the image guided augmented reality method according to the present invention. FIG. 2 is a diagram showing the coordinate relationship of the system architecture of FIG. 1 of the present invention. Wherein, a camera 10 is located in the vicinity of a marked point 20, and a surgical operator's eye 30 is located adjacent to the camera 10 and above the marked point 20. Since the surgical operator wears a wearable glasses, the screen 40 of the wearable glasses is present between the eye 30 and the marked point 20.

The image guided augmented reality method, used for obtaining a correct position of an eye to a marked point, the image guided augmented reality method comprising the following steps of:

step 1: obtaining a first conversion matrix of a camera and a marked point;

step 2: obtaining a second conversion matrix of the eye and the camera;

step 3: linking the first conversion matrix and the second conversion matrix to obtain a correct position corresponding matrix of the eye to the marked point; and step 4: linking the correct position corresponding matrix to a position feature of the marked point to obtain the correct position of the eye to the marked point.

It should be noted that the value of the first conversion matrix $M_{mc}$ of the camera 10 and the marked point 20 is varied, but can be obtained by the camera 10; the value of the second conversion matrix $M_{ce}$ of the eye 30 and the camera 10 is fixed, but the value is unknown, and calibration is performed through a plurality of corner points of the marked point to obtain the value of the second conversion matrix $M_{ce}$. The value of the correct position corresponding matrix $M_{me}$ is variable and unknown, and can be obtained by multiplying the first conversion matrix $M_{mc}$ by the second conversion matrix $M_{ce}$.

Please refer to FIG. 2 at the same time. In step 1, obtaining the first conversion matrix $M_{mc}$ uses a first library to detect the position feature of the marked point and uses a first mathematical operation for the position feature of the marked point to obtain the first conversion matrix $M_{mc}$. Where Xc, Yc, Zc are the coordinates of the camera, as shown in matrix (1); and Xm, Ym, Zm are the position features of the marked point, that is, the coordinates of the marked point.

$$\begin{bmatrix} X_c \\ Y_c \\ Z_c \\ 1 \end{bmatrix} \begin{bmatrix} v_{11} & v_{12} & v_{13} & w_x \\ v_{21} & v_{22} & v_{23} & w_y \\ v_{31} & v_{32} & v_{33} & w_z \\ 0 & 0 & 0 & 1 \end{bmatrix} \begin{bmatrix} X_m \\ Y_m \\ Z_m \\ 1 \end{bmatrix} = \quad (1)$$

$$\begin{bmatrix} V_{3\times3} & W_{3\times1} \\ 0 \quad 0 \quad 0 & 1 \end{bmatrix} \begin{bmatrix} X_m \\ Y_m \\ Z_m \\ 1 \end{bmatrix} = M_{mc} \begin{bmatrix} X_m \\ Y_m \\ Z_m \\ 1 \end{bmatrix}$$

Please refer to FIG. 2. In step 2, obtaining the second conversion matrix of the eye and the camera further comprises the following steps of:

step 21: wearing a glasses and selecting a plurality of corner points of the marked point to obtain a two-dimensional coordinate on a screen of the glasses;

step 22: using a second library to obtain a three-dimensional coordinate corresponding to the camera, to obtain the second conversion matrix Mce of two-dimensional coordinate and the camera by a second mathematical operation, as shown in matrix (2); wherein $(u_i, v_i, w_i)$ is a two-dimensional coordinate on the screen, which has different corresponding coordinate values according to a plurality of corner points of the marked point; and $(X_i^w, Y_i^w, Z_i^w)$ is the three-dimensional coordinate of the camera, which has different corresponding coordinate values according to the plurality of corner points of the marked point;

$$\begin{pmatrix} u_i \\ v_i \\ w_i \end{pmatrix} = M_{ce} \begin{pmatrix} X_i^w \\ Y_i^w \\ Z_i^w \\ 1 \end{pmatrix} = \begin{bmatrix} m_{11} & m_{12} & m_{13} & m_{14} \\ m_{21} & m_{22} & m_{23} & m_{24} \\ m_{31} & m_{32} & m_{33} & m_{34} \end{bmatrix} \begin{pmatrix} X_i^w \\ Y_i^w \\ Z_i^w \\ 1 \end{pmatrix} \quad (2)$$

step 23: using a de-coupling equation to obtain the second conversion matrix.

Wherein, the plurality of corner points of the marked point are at least 8 corner points, preferably, the plurality of corner points of the marked point are 12 corner points. The first library and the second library are ArToolKit libraries written in C/C++ language or libraries such as Auroco or ooopds.

The surgical navigation method of wearable glasses, comprising the following steps of:

step 100: before the operation, making a tomographic image of more than one marked point in the affected part;

step 200: making the tomographic image into a three-dimensional stereoscopic simulated image;

step 300: using an image guided augmented reality method to obtain a correct position of an operator's eye to the marked point of the affected part to adjust the error of the three-dimensional stereoscopic image and the marked point;

Wherein, the step 300, the image guided augmented reality method comprises the following steps of:

step 310: obtaining a first conversion matrix of a camera and a marked point;

step 320: obtaining a second conversion matrix of the eye and the camera;

step 330: linking the first conversion matrix and the second conversion matrix to obtain a correct position corresponding matrix of the eye to the marked point; and step 340: linking the correct position corresponding matrix to a position feature of the marked point to obtain the correct position of the eye to the marked point.

The tomographic image may include a computerized tomography (CT), a magnetic resonance image (MRI), an X-ray, a nuclear medical image, and the like to reconstruct a 3D non-immediate image model.

Because the visual focus of the human eye as seen from the glasses has an error value from the distance of the actual object from the eye, the present invention would solve this problem. Before the operation, the operator, that is, the surgeon, wears the glasses (that is, the computer-aided glasses), and then tests the eye 30 depending on the focal length of the glasses, with a plurality of, usually 8 or more, preferably 12 detection points. After calculation, the error value of the visual focal length is fed back to the computer system for calculation, and the obtained adjusted focal length value is adjusted according to the three-dimensional stereoscopic simulated image obtained in steps 100 and 200, and projected on the screen 40 of the computer-aided glasses. In this way, accurate 3D simulated images of the vision in the affected part can be obtained.

In step 310, obtaining the first conversion matrix $M_{mc}$ uses a first library to detect the position feature of the marked point and uses a first mathematical operation for the position feature of the marked point to obtain the first conversion matrix $M_{mc}$, as shown in matrix (1).

In step 322, obtaining the second conversion matrix of the eye and the camera further comprises the following steps of:

step 321: wearing a glasses and selecting a plurality of corner points of the marked point to obtain a two-dimensional coordinate on a screen of the glasses;

step 322: using a second library to obtain a three-dimensional coordinate corresponding to the camera, to obtain the second conversion matrix Mce of two-dimensional coordinate and the camera by a second mathematical operation, as shown in matrix (2);

step 323: using a de-coupling equation to obtain the second conversion matrix.

Wherein, the plurality of corner points of the marked point are at least 8 corner points, preferably, the plurality of corner points of the marked point are 12 corner points. The first library and the second library are ArToolKit libraries written in C/C++ language or libraries such as Auroco or ooopds.

The present invention overcomes the problem of establishing a basic image method by the proposed mage guided augmented reality method. In clinical trials, a three-dimensional model of a patient is used to illustrate the proposed basic image recording method and to find the entry point for a full-scale surgical procedure. The results of the experiment showed that two surgeons used the proposed mage guided augmented reality system in four spine operations, which was 70% time shorter than when the C-arm was used to guide the needle to the target entry point. The main reason is that the image using the proposed method will be directly applicable to the glasses, and the surgeon only needs to look at the patient without paying attention to the C-arm screen. These tests show that the system works flawlessly in the operating room and provides useful information, especially for spinal surgery to find entry points. For accurate evaluation, 20 sets of entry points were used on the simulated dummy and the ARCAGO system was used to simulate the lumbar puncture procedure in four experiments. In the case of dynamic operation, the average error distance is 2.2±0.25 mm.

The present invention is directed to a surgical navigation method of wearable glasses. In clinical trials, the stereo calibration accuracy of both eyes is ≤1.5 mm; the clinical calibration time is ≤3 minutes. The point accuracy of the marked point is ≤1 mm, and the execution speed of the positioning is at 30 fps. The 3D stereo image model has an offset stability of mm 1.5 mm and an execution speed of 30 fps.

According to the disclosure of the present invention, the present invention has the following advantages of reducing the operation time, reducing the amount of X-ray usage, less radiation, and assisting the positioning of the surgery.

While the invention has been disclosed in the foregoing preferred embodiments, they are not intended to limit the present invention, and one skilled in the art, without departing from the spirit and scope of the present disclosure, may make various changes or modifications. Therefore the scope of the present invention is best defined by the appended claims.

What is claimed is:

1. An image guided augmented reality method, used for obtaining a correct position of an eye to a marked point, the image guided augmented reality method comprising the following steps of:
   obtaining a first conversion matrix of a camera and a marked point;
   obtaining a second conversion matrix of the eye and the camera;
   linking the first conversion matrix and the second conversion matrix to obtain a correct position corresponding matrix of the eye to the marked point; and
   linking the correct position corresponding matrix to a position feature of the marked point to obtain the correct position of the eye to the marked point,
   wherein obtaining the second conversion matrix of the eye and the camera comprises the following steps of:
      wearing a glasses and selecting a plurality of corner points of the marked point to obtain a two-dimensional coordinate on a screen of the glasses;
      using a second library to obtain a three-dimensional coordinate corresponding to the camera, to obtain the second conversion matrix of two-dimensional coordinate and the camera by a second mathematical operation; and
      using a de-coupling equation to obtain the second conversion matrix.

2. The image guided augmented reality method according to claim 1, wherein obtaining the first conversion matrix uses a first library to detect the position feature of the marked point and uses a first mathematical operation for the position feature of the marked point to obtain the first conversion matrix.

3. The image guided augmented reality method according to claim 1, wherein the value of the correct position corresponding matrix is variable and unknown, and is obtained by multiplying the first conversion matrix by the second conversion matrix.

4. The image guided augmented reality method according to claim 1, wherein the plurality of corner points of the marked point are at least 8 corner points.

5. The image guided augmented reality method according to claim 1, wherein the plurality of corner points of the marked point are 12 corner points.

6. A surgical navigation method of wearable glasses, comprising the following steps of:
   before the operation, making a tomographic image of more than one marked point in the affected part;
   making the tomographic image into a three-dimensional stereoscopic simulated image;
   using an image guided augmented reality method to obtain a correct position of an operator's eye to the marked point of the affected part to adjust the error of the three-dimensional stereoscopic image and the marked point;
   wherein the image guided augmented reality method comprises the following steps of:
      obtaining a first conversion matrix of a camera and a marked point;
      obtaining a second conversion matrix of the eye and the camera;
      linking the first conversion matrix and the second conversion matrix to obtain a correct position corresponding matrix of the eye to the marked point; and
      linking the correct position corresponding matrix to a position feature of the marked point to obtain the correct position of the eye to the marked point,
   wherein obtaining the second conversion matrix of the eye and the camera further comprises the following steps of:
      wearing a glasses and selecting a plurality of corner points of the marked point to obtain a two-dimensional coordinate on a screen of the glasses;
      using a second library to obtain a three-dimensional coordinate corresponding to the camera, to obtain the second conversion matrix of two-dimensional coordinate and the camera by a second mathematical operation; and
      using a de-coupling equation to obtain the second conversion matrix.

7. The surgical navigation method of wearable glasses according to claim 6, wherein obtaining the first conversion matrix uses a first library to detect the position feature of the marked point and uses a first mathematical operation for the position feature of the marked point to obtain the first conversion matrix.

8. The surgical navigation method of wearable glasses according to claim 6, wherein the value of the correct position corresponding matrix is variable and unknown, and is obtained by multiplying the first conversion matrix by the second conversion matrix.

9. The surgical navigation method of wearable glasses according to claim 6, wherein the plurality of corner points of the marked point are at least 8 corner points.

10. The surgical navigation method of wearable glasses according to claim 6, wherein the plurality of corner points of the marked point are 12 corner points.

* * * * *